United States Patent [19]

Boryta

[11] Patent Number: 4,985,682
[45] Date of Patent: Jan. 15, 1991

[54] LEAK MONITOR FOR SECONDARY CONTAINMENT OF LIQUID STORED IN UNDERGROUND STORAGE TANKS

[75] Inventor: Daniel A. Boryta, Downington, Pa.

[73] Assignee: Leak Sensors, Inc., West Hartford, Conn.

[21] Appl. No.: 932,795

[22] Filed: Nov. 20, 1986

[51] Int. Cl.⁵ .................... G01N 27/04; G08B 21/00
[52] U.S. Cl. .................... 324/557; 340/605; 340/606
[58] Field of Search ............... 324/522, 523, 525, 541, 324/544, 551, 553, 554, 557-559, 65 R, 425, 450; 340/603-606; 73/1 R, 1 H, 3

[56] References Cited

U.S. PATENT DOCUMENTS

| | | | |
|---|---|---|---|
| 3,383,863 | 5/1968 | Berry | 324/54 X |
| 3,405,356 | 10/1968 | Hubby | 324/54 |
| 3,789,297 | 1/1974 | Frolich | 324/65 R |
| 3,800,217 | 3/1976 | Lowrance | 324/54 |
| 3,858,114 | 12/1975 | Voellmin et al. | 324/425 X |
| 4,101,827 | 7/1983 | Offner | 324/65 R |
| 4,404,516 | 9/1983 | Johnson, Jr. | 324/54 |
| 4,543,525 | 9/1985 | Boryta et al. | 324/54 |
| 4,568,925 | 2/1986 | Butts | 340/605 |
| 4,720,669 | 1/1988 | Owen | 324/546 |

OTHER PUBLICATIONS

Petroleum Marketer, Nov.-Dec. 1985, pp. 23 and 24.
Niaki et al, Project Summary "Underground Tank Leak Detection Methods, A State-of-the-Art Review", EPA/600/S2-86/001, Jul. 1986.

Primary Examiner—Reinhard J. Eisenzopf
Assistant Examiner—Jack B. Harvey
Attorney, Agent, or Firm—Howson & Howson

[57] ABSTRACT

A system for monitoring the continuity and potential rate of leakage of an underground tank hole liner formed of a sheet of electrically insulating polymeric material in which a standard current measurement is made of a circuit comprising a standard electrode in the form of a container of electrically insulating material having a small hole in a side thereof and containing an electrically conductive fluid connected to an injection electrode through a current source, the electrodes being immersed in a conductive fluid in the bottom of the tank hole to provide a calibrated liner leakage value, and such measurement is compared with the current provided by a circuit comprising the injection electrode connected to a ground electrode through the current source. If the latter current measurement is less than the standard, the area of the liner tested is considered to meet specifications as regards leakage since the total area of leaks, if any, is no greater than the area of the hole in the standard electrode, where as if the current exceeds the standard value, the liner is deemed not to meet specifications.

21 Claims, 2 Drawing Sheets

LEAK MONITOR FOR SECONDARY CONTAINMENT OF LIQUID STORED IN UNDERGROUND STORAGE TANKS

1. GENERAL DESCRIPTION OF THE INVENTION

The present invention relates generally to prevention of pollution of earth and ground water by hazardous chemicals, and especially a system and method for monitoring the continuity and potential rate of leakage of storage tank hole liners designed to provide secondary containment of liquid petroleum products and the like leaking from underground storage tanks to prevent pollution of soil and ground water.

2. BACKGROUND OF THE INVENTION

A particularly serious problem is contamination of ground water with gasoline and other liquid petroleum products by reason of leaks in underground storage tanks. Estimates from government and industrial sources are that between 1.25 and 3.4 million underground storage tanks exist in the nation and that from 75,000 to 100,000 are leaking. In addition, it is estimated that as many as 350,000 others may develop leaks in the next few years. In view thereof secondary containment liners for underground petroleum storage tanks are being used, and it is important that such in ground liners, which are made of hydrocarbon-resistant polymeric material, be monitored for leaks.

Thus, the State of California for instance requires that all underground gasoline and fuel storage tanks be provided with a secondary confinement system to prevent leakage of petroleum products into the ground upon failure of the primary storage tanks. In addition, an approved method of monitoring the continuity of the secondary confinement system will soon be required. At the present time double-walled tanks with leak monitoring capability are available, but monitoring of leaks in tank piping is presently unavailable. Although the secondary confinement system does provide protection of ground water against leaks in piping as well as in the storage tanks a monitoring system to determine the presence of leaks and rate of leaking of the secondary confinement system prior to the present invention has been unavailable.

Man-made waste disposal ponds for storage of environmentally hazardous materials, such as chemical wastes, are commonly used today. These ponds are usually lined with a polymeric sheet material to prevent the hazardous chemicals from contaminating earth and ground water.

It is an object of the present invention to provide a novel system and method for monitoring the continuity of underground liners designed to provide secondary confinement of liquid petroleum products stored in underground storage tanks.

It is another object of the present invention to provide a method and system for monitoring the potential rate of leakage of underground liners designed to provide secondary confinement of liquid petroleum products stored in underground storage tanks.

Another object of this invention is to provide a method and system for detecting potential leaks in pond liners of electrically insulating material prior to introducing to the pond the liquid to be retained therein.

Yet another object of the invention is to provide a method and system of monitoring for leaks liners for ponds containing hazardous liquids.

These and other objects of this invention will become further apparent from the following description, appended claims and drawings in which:

3. GENERAL DESCRIPTION OF THE INVENTION

The invention in general terms is directed to monitoring of leaks in liners for ponds and the like designed to prevent hazardous chemicals from polluting earth and ground water and particularly to a system and method of monitoring both continuity and potential rate of leakage of a liner of a secondary confinement system for underground fuel storage tanks comprising in combination with a secondary confinement system consisting of a tank hole liner formed of a sheet of electrically insulating polymeric material, at least two inspection wells extending from the ground surface into a layer of water located at the bottom of the hole and within the liner, at least one ground electrode exterior of the hole and liner, a standard electrode comprising a container of insulating material having a hole of known dimensions in a wall thereof for containing an electrically conductive aqueous fluid and an injection electrode, a current source, and means for monitoring at least one electrical property of the circuit comprising said standard electrode, current source, and either the ground electrode or the injection electrode.

Figure 1:
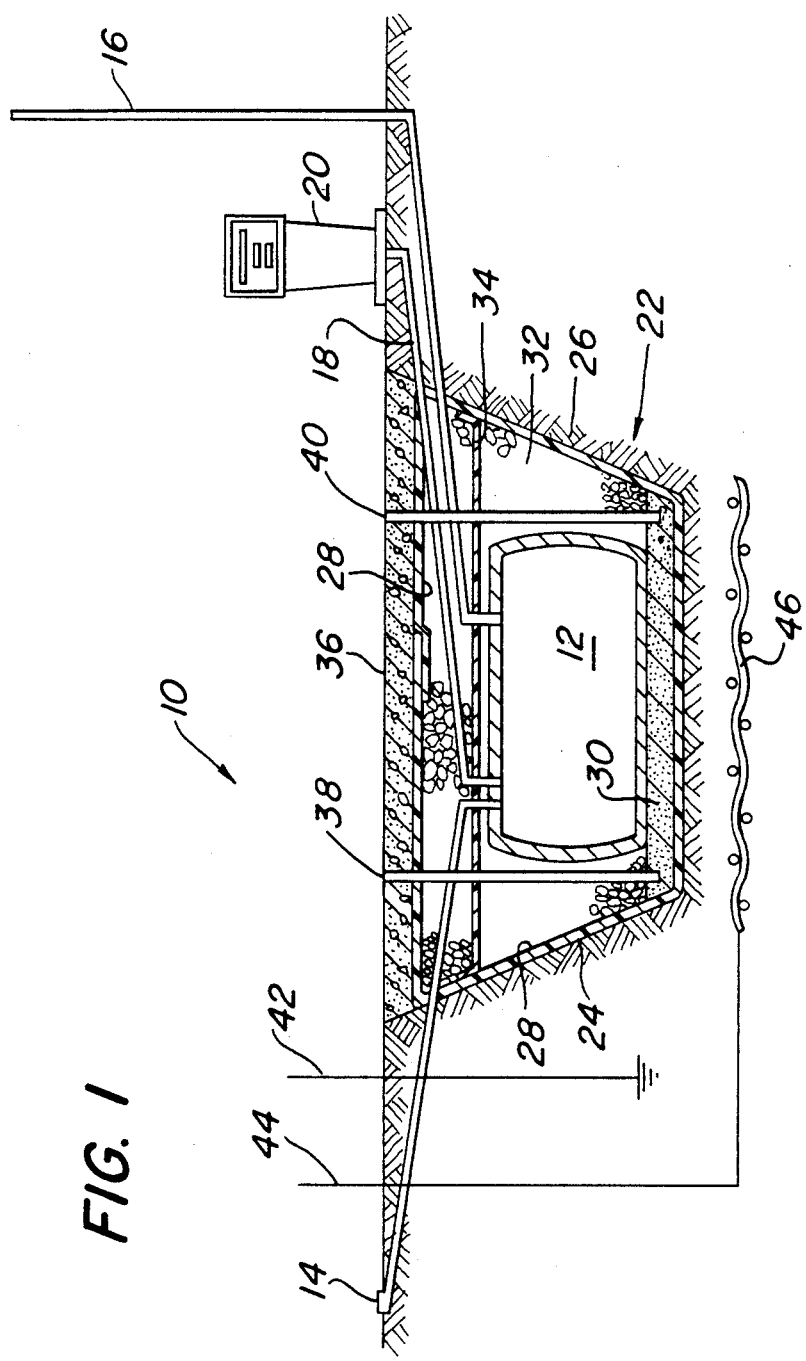
FIG. 1 is a schematic view illustrating a secondary confinement system for underground storage of liquid petroleum products including the leak monitoring means of this invention.

In use the standard electrode filled with an electrically conductive aqueous fluid and the injection electrode are lowered to the bottom of their respective wells so as to be in contact with the layer of water at the bottom of the tank hole and within the hole liner. Where there are two ground electrodes exterior the tank hole and liner as shown in FIG. 1, the ground connection may first be tested by establishing an electrical potential between the two electrodes and measuring the current. The resistivity of the hole of known dimensions in the standard electrode is then calibrated by establishing an electrical potential between the standard and injection electrodes and measuring the current in such circuit which includes the water layer at the bottom of the tank hole. Next the injection electrode is connected to a ground electrode, an electrical potential is established between the two electrodes and the current in the circuit comprising the two electrodes the conductive layer of soil beneath the tank hole and the water in the bottom of the tank hole is measured If the current reading is less than that provided using the circuit comprising the standard and injection electrodes, the liner is either free of holes or at least meets specifications as far as leakage is concerned, for the total area of any holes in the liner is less than that of the hole in the standard electrode. However, if the current caused by the total area of any holes in the liner is greater than that provided by the hole in the standard electrode, the liner is considered to provide insufficient secondary containment of the hazardous liquid.

Figure 3:
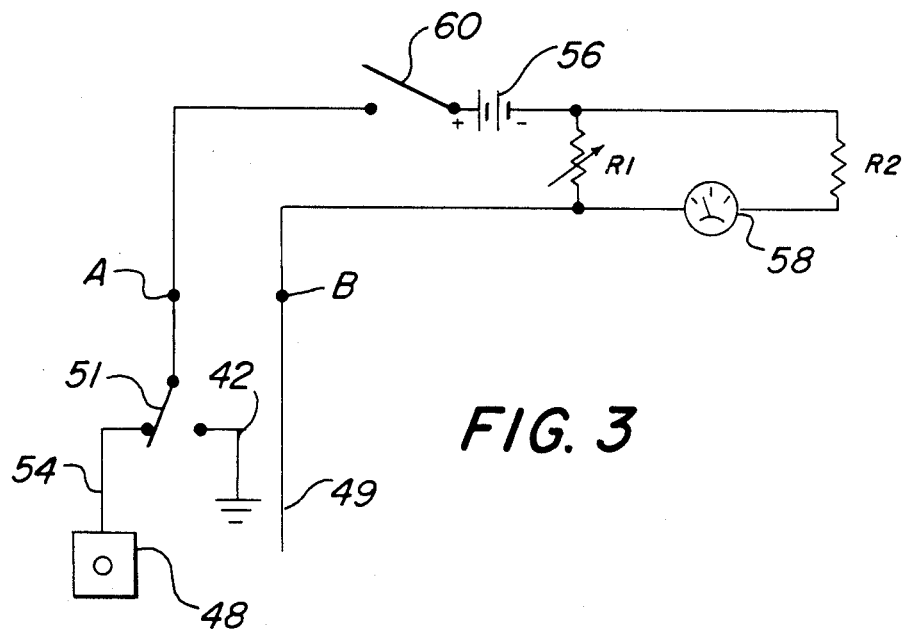
FIG. 3 is a simplified diagram of electrical circuitry which may be used in the leak monitoring system of the invention.

By appropriate calculations using the empirical formula $$(\text{Hole Area Std. Electrode, mm}^2) \times \frac{R_1(\text{Std.})}{R_1(\text{Unknown})} \times \frac{\mu A(\text{unknown})}{\mu A(\text{Std.})} = (\text{Area of Unknown Hole, mm}^2)$$

where $R_1$ is the resistance of the resistor $R_1$ in FIG. 3, and $\mu A$ is the current in microamps of the monitoring circuit, the total area of the hole or holes in the liner can be calculated.

DESCRIPTION OF A PREFERRED EMBODIMENT

Referring to the drawings, FIG. 1 shows a typical underground petroleum storage tank installation 10 including secondary containment means for the liquid in the storage tank. Such underground storage facilities usually contain a plurality of tanks, e.g. three or more; however, for the sake of simplicity only a single tank is shown in FIG. 1.

Considering the installation in greater detail, tank 12 may be of the conventional double walled type having the usual access pipes connected to the top side of the tank. These pipes include a fill pipe 14, vent pipe 16, and an interconnecting conduit 18 to a fuel pump 20 located above ground.

Storage tank 12 is located in a tank hole or excavation 22 which is basically rectangular in shape and of sufficient depth to house tank 10 below the surface of the ground. The side walls of the tank hole, such as side walls 24 and 26 are sloped inwardly to the desired degree to minimize the possibility of their collapse. The bottom, side walls and top of the tank hole or excavation 22 are lined with a sheet of electrically insulating polymeric material 28, such as a polyester elastomer sold under the trademark Hytrel ® by E. I. duPont de Nemours & Co., Inc. which polymer is resistant to petroleum hydrocarbons. However, the liner may be of any suitable polymeric material, e.g. polyvinyl chloride, provided it is electrically insulating and chemically resistant to the liquid being stored. The sheet ordinarily will have a thickness of from about 20 to 80 mils and may comprise a number of strips bonded together in an overlapping relation along their adjacent edges. Such seams have been found to be a particularly annoying source of leaks.

The purpose of the liner 28 is to provide for secondary containment of any liquid which leaks from the storage tank 12 or pipes connected thereto, so as to prevent pollution of the soil and ground water in the area near the tank.

Those portions of the pipes exterior of the tank hole may also be provided with trench lines of polymeric sheet material connected to the tank hole liner so that any fluid which leaks from the pipes will run into the secondary containment.

Beneath the storage tank 12 there is a base layer of footing material 30, which preferably is a layer of packed sand about a foot in depth. The sand is saturated with water to a depth of 6 or more inches. Where the side walls of the liner are to be checked for leaks, the water level should be sufficiently high to cover all areas to be tested.

The tank 12 is encased with fill material 32 such as pea gravel Also extending across the excavation 22 immediately above the tank 12 is a layer or sheet 34 of electrically insulating polymeric material, which may be of the same composition as the liner 28, and is preferably bonded to the liner along its peripheral edges.

When so installed, and properly connected to the conduits 14, 16 and 18, the tank 12 is insulated from ground.

A poured reinforced concrete top slab 36 is positioned over the excavation to complete the installation 10.

Extending substantially vertically from the ground surface and through the top slab and into the base layer of sand are two spaced inspection wells 38 and 40 which are also insulated from ground. However, any number of inspection wells may be present depending upon the size of the tank hole, a greater number being used with large size holes containing several tanks. The function of these inspection wells is discussed in greater detail hereinbelow.

Again referring to FIG. 1 there are illustrated two ground electrodes 42 and 44 which are located adjacent to but exterior of the storage tank hole and liner Ground electrode 42 can be merely a heavy cable or post of electrically conductive material which provides a good electrical ground connection with the soil, which also should have some electrical conductivity. Electrode 44 comprises a conductive cable which is connected to a conductive metal screen 46 of relatively open mesh, e.g. a screen having a $1' \times 1'$ mesh size. The function of the ground electrodes is also discussed subsequently.

Figure 2:
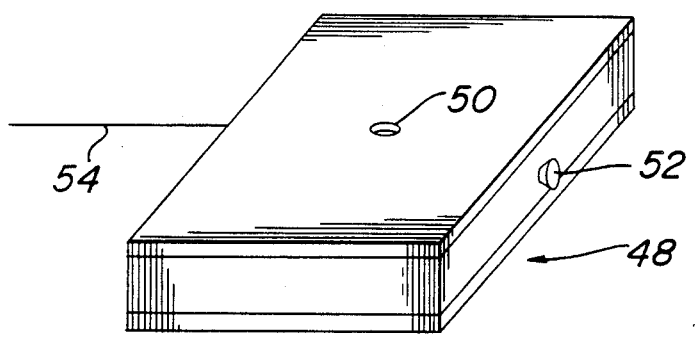
FIG. 2 is a perspective view of a standard electrode for use in the leak monitoring system of the invention.

Referring to FIG. 2, there is illustrated a standard electrode 48 in the form of a hollow rectangular container of suitable nonconductive material, such as clear plastic, the dimensions of which are sufficiently small to permit the electrode to be inserted in one of the inspection wells. In one face of the electrode is a hole 50 of known dimensions, e.g. 1 to 10 mm in diameter. The size of the hole is important since, as will be seen, it provides the calibration for determining whether the liner is acting as satisfactory secondary containment even though there may be slight leakage of the stored liquid into the ground. In one edge of the electrode is a second or fill hole in which a plug or stopper 52, which may be of rubber or the like, is seated. The interior of the electrode 48 is connected to an electrically conductive wire 54 of sufficient length to lower the electrode to the bottom of an inspection well to contact the water layer. The standard electrode 48 is filled with an electrically conductive liquid which is preferably the same as the layer of water at the bottom of the tank hole.

The injection electrode which is introduced into the other of the two inspection wells may be merely an electrical conductor in the form of an exposed wire 49 as seen in FIG. 3.

In FIG. 3, there is shown a simplified electrical circuit for monitoring the liner 28 for continuity and rate of leakage. The system there shown comprises a current source 56, which may be a 12 volt battery, connected to means for monitoring an electrical property of the circuit, such as microammeter 58 connected in series to the fixed resistor, $R_2$, and parallel to the variable resistor, $R_1$. Satisfactory readings can be obtained if $R_2$ has a resistance of about 100 K ohms and the resistance of $R_1$ varies from 0 to about 100 K ohms. The circuit is also provided with an on-off switch 60. The leads A and B of the circuit are designed to be connected to the ground electrodes 42, 44 and/or the standard and injection electrodes by appropriate switch means, not shown.

In using the system for detecting a leak, the standard calibrated electrode is filled with an aqueous solution, usually water from the bottom of the tank hole, which is electrically conductive, and is lowered to the bottom of one of the wells 38 or 40. The injection electrode is lowered to the bottom of the other of the two inspection wells. Each of the two electrodes should be in contact with the water in the layer of footing material 30.

Before proceeding with the test, the two ground electrodes 42 and 44 are checked to determine whether each provides a satisfactory ground connection. This is accomplished by connecting one of leads A and B of the circuit illustrated in FIG. 3 to one of the ground electrodes 42, 44, and the other lead to the other ground electrode, closing the switch 60 and noting the reading on the microammeter.

After testing of the ground connections, one of leads A or B is connected to the standard electrode and the other to the injection electrode. To calibrate the microammeter for a specific hole area, i.e. the area of the hole on the standard electrode, resistance $R_2$ is adjusted so that the microammeter gives a predetermined reading such as the center point of the dial. The hole of known dimensions in the standard electrode provides a specific resistance which should be related to the total permissible leakage of the liner area to be tested.

To test an area of the liner for a leak and the rate of leakage, the injection electrode 49 is then connected to one of terminals A and B, the other terminal is connected through a switch 51, first to the standard electrode 48 for a first cablibrated reading, and then to one of the ground electrodes 42, 44, whereupon a meter reading is made. If the meter gives a lower current reading than the calibrated reading provided by the standard electrode, the liner continuity is considered to meet specifications, e.g. 0.15 gallons/hour maximum under EPA regulations. On the other hand, if the reading on the meter is greater than the specified calibration mark based on use of the standard electrode, the liner is considered as not meeting the leak rate specification.

It is important that a proper water level be maintained in the bottom of the tank hole otherwise a false low reading may be given as the result of an absence of conductive fluid. Thus, prior to testing for a leak, the standardized test should be run.

Advantageously the system can be used to determine the total area of a single hole or several holes in the area of the liner 28 which is tested. Such determination is demonstrated by the following example using a 1 mm diameter hole as the unknown and a standard electrode having a ¼" diameter hole.

|  | Hole Dimensions | | Resistance (ohms) | | Current |
|---|---|---|---|---|---|
|  | Diameter (mm) | Area (mm²) | $R_1$ | $R_2$ | Micro Amps |
| Standard | 6.34 | 31.67 | 1K | 100K | 20 |
| Unknown | 1.0 | 0.78 | 50K | 100K | 22 |

Using the following empirical formula, the area of the unknown hole is determined as follows:

$$(\text{Area Std. Hole, mm}^2) \times \frac{R_1(\text{Std.})}{R_1(\text{Unknown})} \times$$

$$\frac{\mu A(\text{Unknown})}{\mu A(\text{Std.})} = (\text{Area Unknown Hole, mm})$$

Using the values for resistance and current set forth in the above table in the formula, the area of the unknown hole may be calculated as follows:

$$31.67 \times \frac{1}{50} \times \frac{22}{20} = 0.70 \text{ mm}^2$$

As can be seen the formula and method provide a good approximation of the area of the hole, i.e. 0.70 mm² v. 0.78 mm².

The principle on which the above formula is predicated is that resistance is inversely proportional to hole area, and that the liner 28 has an electrical resistance orders of magnitude higher than both ground and the water layer within the liner. However, if the liner resistance becomes a factor, i.e., when monitoring a large pond for potential leaks (1–6 acres), the calibration circuit will have a resistance installed connected between A and B (FIG. 3) and this resistance will match the liner resistance.

From the foregoing discussion it can be seen that the system and method of the present invention make possible continuous monitoring of a tank hole liner for continuity and integrity and potential leak rate, whereby necessary steps can be taken to prevent environmentally adverse liquids from permeating and polluting ground water.

Although the system and method of this invention is particularly useful in monitoring the integrity of secondary confinement systems for underground storage tanks for fuels and the like, they may also be used in any compoundment for liquid toxic wastes and the like in the form of a ground excavation provided with a liner of electrically insulating polymeric sheet material which is chemically resistant to the liquid waste stored therein.

I claim:

1. In a pond having a liner formed of electrically insulating polymeric material, and containing a layer of conductive liquid, a system for monitoring the continuity and for determining the rate of leakage of the liner which comprises a standard electrode and an injection electrode spaced from each other and in contact with said liquid, said standard electrode comprising a container of electrically insulating material for containing an electrically conductive liquid and having a hole in a wall thereof of predetermined dimensions through which the conductive liquid can contact said liquid in said pond, a ground electrode external of said pond and liner, a current source, means for monitoring resistance in an electrical circuit, and means for alternatively establishing a first electrical circuit comprising said injection electrode, said current source, said monitoring means and said standard electrode in series and a second electrical circuit comprising said injection electrode, said current source, said monitoring means and said ground electrode in series.

2. The system of claim 1 in which said ground electrode comprises an electrically conductive open mesh screen.

3. The system of claim 1 in which the hole in said container comprising said standard electrode has a diameter of from about 1 mm to 10 mm.

4. The system of claim 1 in which the conductive liquid in said standard electrode is the same as that in said pond.

5. The system of claim 4 in which said conductive liquid is an aqueous solution of a water soluble salt.

6. A method for determining whether a liner of a ground excavation permits an electrically conductive liquid contained therein to leak through it into the soil which comprises introducing to said liquid a standard electrode and an injection electrode, said standard electrode comprising a container of electrically insulating material having a hole in a surface thereof, said hole having an area no greater than the permissible total area of all leaks in the area of the liner to be tested, forming a first circuit in which said electrodes are connected to a current source to provide an electric potential between said electrodes and measuring the resistance of the portion of said first circuit comprising the standard electrode, the injection electrode and the path between them, providing a second circuit in which said injection electrode is connected to a ground electrode through said current source to provide an electric potential between said injection electrode and said ground electrode, measuring the resistance of the portion of said second circuit comprising the injection electrode, the ground electrode and the path between them, and comparing the resistance measured in said second circuit with that of said first circuit.

7. The method of claim 6 in which the liquid contained in said excavation and in said standard electrode comprises water.

8. In a secondary confinement system for protecting ground water from a potentially hazardous liquid stored in an underground storage tank and in which said tank is located in a tank hole lined with a sheet of electrically insulating polymeric material which is chemically resistant to the stored liquid, the improvement which comprises a system for monitoring the continuity of said sheet material and for determining the rate of leakage thereof, said system comprising an aqueous layer on the bottom of said hole and within said liner, at least two inspection wells extending from the earth's surface into said aqueous layer, a standard electrode in one of said wells and an injection electrode in the other of said wells, said electrodes being in contact with said aqueous layer, said standard electrode comprising a container of electrically insulating material for containing an electrically conductive aqueous fluid and having a hole in a wall thereof of predetermined dimensions through which said conductive fluid can contact said aqueous layer, a ground electrode external of said hole and liner, a current source, means for monitoring resistance in an electrical circuit, and means for alternatively establishing a first electrical circuit comprising said injection electrode, said current source, said monitoring means and said standard electrode in series and a second electrical circuit comprising said injection electrode, said current source, said monitoring means and said ground electrode in series.

9. The secondary confinement system of claim 8 in which said ground electrode comprises an electrically conductive open mesh screen.

10. The secondary confinement system of claim 8 in which the hole in said container comprising said standard electrode has a diameter of from about 1 mm to 10 mm.

11. The system of claim 8 in which the conductive fluid in said standard electrode is the same as that in said aqueous layer.

12. The system of claim 11 in which said conductive fluid is an aqueous solution of a water soluble salt.

13. A method of monitoring the continuity and rate of leakage of a secondary confinement system for protecting ground water from a potentially hazardous liquid stored in an underground storage tank located in a tank hole, said secondary confinement system comprising a liner for said tank hole composed of a sheet of electrically insulating polymeric material which is chemically resistant to the stored liquid, which method comprises maintaining in the bottom of said tank hole and within said liner a layer of a conductive fluid, introducing into said tank hole so as to contact said layer of conductive fluid spaced standard and injection electrodes, said standard electrode comprising a container of electrically insulating material having a hole of predetermined size located in a wall thereof, said container containing an electrically conductive fluid, providing a first circuit comprising said standard electrode, a current source and said injection electrode, establishing an electric potential between said electrodes, and measuring the resistance of the portion of said first circuit comprising the injection electrode, the standard electrode and the path between them, providing a second circuit comprising said injection electrode, a current source and ground, establishing an electric potential between said injection electrode and ground, measuring the resistance of the portion of said second circuit comprising the injection electrode, ground and the path between the injection electrode and ground, and comparing the two measurements.

14. The secondary confinement system of claim 13 in which said ground electrode comprises an electrically conductive open mesh screen.

15. The secondary confinement system of claim 13 in which the hole in said container comprising said standard electrode has a diameter of from about 1 mm to 10 mm.

16. The system of claim 13 in which the conductive fluid in said standard electrode is the same as that in said aqueous layer 17. The system of claim 16 in which said conductive fluid is an aqueous solution of a water soluble salt.

18. A method of detecting leakage in the liner of a ground excavation containing an electrically conductive liquid wherein the contents of the liner are electrically isolated by the liner from the soil surrounding the excavation when the liner is intact, comprising:
(a) locating first and second electrode in said liquid in spaced relationship to each other and locating a third electrode in the ground outside the liner; and
(b) comparing the electrical resistance between said first and second electrodes with the electrical resistance between said first and third electrodes.

19. A method according to claim 18 in which the second electrode includes a predetermined resistance substantially equal to the resistance of the maximum permissible leakage hole area in the liner.

20. A method according to claim 19 in which the liner is the liner of a secondary confinement system surrounding a storage tank located within the excavation, and in which the first and second electrodes are introduced into said electrically conductive liquid respectively through first and second wells located adjacent to said storage tank.

21. A method of detecting leakage in the linear of a ground excavation containing an electrically conductive liquid wherein the contents of the liner are electrically isolated by the liner from the soil surrounding the excavation when the liner is intact, comprising:

(a) introducing first and second electrodes into said liquid in spaced relationship to each other, connecting the first and second electrodes to a source of electrical current to establish a first circuit including said source, said electrodes, and a path in said liquid between the electrodes and taking a measurement of the resistance of the portion of said first circuit comprising said electrodes and said path;

(b) connecting a source of electrical current to the first electrode and a third electrode located in the ground outside of said liner to establish a second circuit including the last-mentioned source, the first electrode, the third electrode, and a path through the liner between the first and third electrodes, and taking a measurement of the resistance of the portion of the second circuit comprising said first and third electrodes and said path through the liner; and (c) comparing said resistance measurements.

* * * * *